United States Patent [19]

Friederichs et al.

[11] Patent Number: 5,399,736
[45] Date of Patent: Mar. 21, 1995

[54] PROCESS FOR THE PREPARATION OF HIGHLY PURE AROMATIC DIURETHANES AND/OR POLYURETHANES

[75] Inventors: Wolfgang Friederichs, Cologne; Stefan Penninger, Pulheim; Stefan Wershofen, Moenchengladbach, all of Germany

[73] Assignee: Bayer Aktiengesellschaft, Leverkusen, Germany

[21] Appl. No.: 988,659

[22] Filed: Dec. 10, 1992

[30] Foreign Application Priority Data

Dec. 16, 1991 [DE] Germany .................. 41 41 402.0

[51] Int. Cl.⁶ .................................. C07C 125/06
[52] U.S. Cl. .................................. 560/25; 560/158
[58] Field of Search .................................. 560/25, 158

[56] References Cited

U.S. PATENT DOCUMENTS

| | | | |
|---|---|---|---|
| 2,181,663 | 11/1939 | Martin | 260/2 |
| 3,919,278 | 11/1975 | Rosenthal et al. | 260/453 P |
| 4,081,472 | 3/1978 | Tsumura et al. | 260/453 P |
| 4,278,805 | 7/1981 | Merger et al. | 560/25 |
| 4,290,970 | 9/1981 | Merger | 260/453 P |
| 4,369,141 | 1/1983 | Motier | 260/453 P |
| 4,375,000 | 2/1983 | Merger et al. | 560/25 |
| 4,388,238 | 6/1983 | Heitkämper et al. | 260/239 E |
| 4,388,246 | 6/1983 | Sundermann et al. | 260/453 P |
| 4,482,499 | 11/1984 | Merger et al. | 260/453 P |
| 4,611,079 | 9/1986 | Merger | 560/25 |
| 4,692,550 | 9/1987 | Engbert et al. | 560/345 |

FOREIGN PATENT DOCUMENTS 1458595 12/1976 United Kingdom .

*Primary Examiner*—José G. Dees
*Assistant Examiner*—Samuel Barts
*Attorney, Agent, or Firm*—Joseph C. Gil; N. Denise Brown

[57] ABSTRACT

This invention relates to a process for the preparation of highly pure aromatic diurethanes and/or polyurethanes by reaction of the corresponding aromatic diamines and/or polyamines with unsubstituted carbamates with the release of ammonia. The reaction is carried out in the presence of excess carbamates. The resultant reaction mixture is freed from any solvents used, and the formed aromatic diurethanes and/or polyurethanes are purified by extraction with water.

17 Claims, No Drawings

PROCESS FOR THE PREPARATION OF HIGHLY PURE AROMATIC DIURETHANES AND/OR POLYURETHANES

BACKGROUND OF THE INVENTION

The present invention relates to a process for the preparation of highly pure aromatic diurethanes and/or polyurethanes by the reaction of aromatic diamines and/or polyamines with unsubstituted carbamates with the release of ammonia.

The preparation of aromatic diurethanes and/or polyurethanes from aromatic diamines and/or polyamines and unsubstituted carbamates is of great interest as aromatic diurethanes and/or polyurethanes can be converted by thermal decomposition into aromatic diisocyanates and/or polyisocyanates which may be used as starting materials for the production of high quality polyurethane resins. Since the unsubstituted carbamates used as reactants for the preparation of the aromatic diurethanes and/or polyurethanes are obtainable from urea and alcohols, they enable aromatic diisocyanates and/or polyisocyanates to be produced without the use of phosgene.

Processes for the preparation of aromatic diurethanes and/or polyurethanes from aromatic diamines and/or polyamines and unsubstituted carbamates are known and are described in numerous patents (DE 2,942,511, DE 2,917,568, DE 2,943,480, EP 18,583). The processes hitherto employed have the disadvantage that the diurethanes and/or polyurethanes are not obtained in pure form. A high purity is necessary for the successful decomposition of urethanes, and hence for the optimum preparation of aromatic diisocyanates and/or polyisocyanates. The products produced by the known processes generally contain starting materials and/or by-products which are inevitably produced, e.g. aminourethanes, urea urethanes, oligoureas and polyureas. These impurities can only be separated with great difficulty from the products of the process, and therefore, increase the cost of preparation.

One exception are the aromatic diurethanes based on methanol obtained from the reaction of aromatic diamines and methyl carbamate. In general, these urethanes have a high melting point, good crystallization properties, and low solubility in organic solvents. Therefore, in contrast to aromatic diurethanes based on other alcohols, they separate as pure crystalline solids from the reaction mixture or can be separated relatively easily by recrystallization from the unwanted impurities which interfere with the decomposition of urethanes. The high melting point and low solubility of the diurethanes based on methanol have, however, a disadvantageous effect on the use of the end products for the preparation of isocyanates. Conversion of the products of the process into isocyanates is carried out by the thermal decomposition of the underlying urethanes. This decomposition is carried out technically at temperatures above 200° C., in a decomposition apparatus into which the urethanes are continuously introduced in the molten or dissolved state (see e.g. U.S. Pat. No. 4,388,246, U.S. Pat. No. 4,081,472, DE 2,421,503, DE 2,526,193, DE 3,142,627, DE 3,108,990, and DE 3,215,591). This method, however, cannot be carried out with diurethanes based on methanol without serious disadvantages since their high melting point is above the decomposition point, and the low solubility necessitates high degrees of dilution. This results in impairment of the volume/time yield, and a considerable increase in costs in the distillative recovery of the solvent.

Aromatic diurethanes and/or polyurethanes are isolated, e.g. according to the teaching of DE 2,917,568 and EP 18,583, from the crude mixtures obtained from the reaction of aromatic diamines and/or polyamines with carbamates. In this process, any catalysts used are removed and any solid products obtained are filtered off. The alcohol and/or the solvent and the carbamate which is optionally used in excess, are completely or partly distilled off, and the product is obtained by crystallization, precipitation, or recrystallization from other solvents. Thus according to EP 18,583 (Example 36) 2,4-bis-(ethoxycarbonylamino)-toluene is purified by distilling off the alcohol used as solvent and excess ethyl carbamate at a reduced pressure of 10 mbar, and dissolving the residue in methylene chloride, and washing it several times with water. Methylene chloride is then separated off, ethanol is added and the mixture is cooled in a mixture of ice and salt. 2,4-Bis-(ethoxycarbonylamino)-toluene then crystallizes with a melting point of 108° to 110° C. However, the 2,4-bis-(ethoxycarbonylamino)-toluene is unsuitable for the decomposition of urethanes due to its insufficient purity. Analytically pure 2,4-bis-(ethoxycarbonylamino)-toluene has a melting point of 134° C.

It was therefore an object of the present invention to provide a process for the preparation of highly pure aromatic diurethanes and/or polyurethanes suitable for the preparation of aromatic diisocyanates and/or polyisocyanates by the thermal decomposition of urethanes.

It was found that in order to obtain highly pure aromatic diurethanes and/or polyurethanes, the reaction known in the art of aromatic diamines and/or polyamines with unsubstituted carbamates with the liberation of ammonia should be carried out with an excess of carbamates, any solvent used being separated off after completion of the reaction, and the product mixture obtained as residue being extracted with water.

DESCRIPTION OF THE INVENTION

The present invention relates to a process for the preparation of highly pure aromatic di- and/or polyurethanes by reaction of the corresponding aromatic di- and/or polyamines with unsubstituted carbamates with liberation of ammonia, characterized in that the reaction is carried out in the presence of excess carbamate. The resultant reaction mixture is freed from any solvents used, and the aromatic di- and/or polyurethanes obtained therefrom are freed from by-products, excess carbamate and unreacted di- and/or polyamines by extraction with water.

The quantity of carbamate used is preferably from about 2 to 50 mol, more preferably from about 10 to 30 mol, of carbamate per mol of amino group in the aromatic di- and/or polyamines.

Ethyl carbamate, propyl carbamate, isopropyl carbamate, and mixtures thereof are preferred carbamates. In one particular embodiment, unpurified carbamate obtained from the reaction of urea with the corresponding alcohols is used as the carbamate.

The reaction of the aromatic di- and/or polyamines with unsubstituted carbamates is preferably carried out with carbamates prepared in situ, using urea and the corresponding alcohol for the reaction.

Any solvents used for the reaction are preferably removed by distillation.

In a preferred embodiment of the process, any solvent present in the reaction mixture obtained is, optionally, removed and the reaction mixture obtained is extracted by mixing it intensively with water. The ratio of mixture to water is from about 0.2:1 to 10:1, preferably from about 0.8:1 to 2:1, at temperatures of from about 20° to 200° C., preferably from about 50° to 100° C., cooling to temperatures of from about 0° to 100° C., preferably from about 20° to 70° C., and then separating off the di- and/or polyurethanes which are obtained as a liquid or solid phase.

The aromatic di- and/or polyurethanes obtained after extraction are preferably dried and/or recrystallized from organic solvents. Preferred solvents include aromatic hydrocarbons. Most preferred are benzene, toluene, xylene, or mixtures thereof. This is optionally done in the presence of surface-active substances. In particular, surface-active substances include active charcoal, Fuller's earth, aluminum oxide, aluminosilicate, or zeolite.

In one particular embodiment of the process, the aqueous phase which is obtained after the extraction step is cooled to temperatures of from about −5° to 20° C., optionally with stirring. The mixture which separates out, consists mainly of carbamates, aminourethanes, urea urethanes, oligo- and polyureas, and optionally, di- and/or polyamines and di- and/or polyurethanes, is returned to the reaction after separation and drying, optionally, together with alcohols.

The aqueous phase obtained as the mother liquor after separation of the mixture may be used for the extraction together with fresh water.

The invention further relates to the use of the aromatic di- and/or polyurethanes obtained by the process according to the invention as a starting material for the preparation of di- and/or polyisocyanates.

The efficiency of the purification step of the reaction products by extraction with water is surprising. It was not expected that the organic impurities could be extracted with water, especially since the extraction of the reaction products with water according to EP 19853 (Example 36) did not provide products having the required high degree of purity.

The process according to the invention has the advantage that, for example, ethyl carbamate, unreacted starting amine and the other by-products can easily be separated from the product according to the invention under relatively mild conditions, and the resultant aromatic di- and/or polyurethanes are obtained in a highly pure state.

Further advantages of the process according to the invention include the fact that unreacted starting amines, by-products and excess carbamates present in the aqueous phase can be separated from the water together in a single process step, and then returned to the reaction immediately, or optionally, after a separate drying, optionally, together with alcohols. By-products can thus be separated without great technical difficulty and returned to the reaction to be used again.

These by-products mainly consist, as mentioned above, of aminourethanes, urea urethanes, oligoureas and polyureas. In other words, the by-products contain aromatic amino compounds and urea compounds. It is well known that urea derivatives react with alcohols to form urethanes and aromatic amino compounds, and that aromatic amino compounds can be converted into urethanes by the reaction with carbamates and the liberation of ammonia.

The process according to the invention is suitable for the preparation of highly pure aromatic di- and/or polyurethanes. These aromatic di- and/or polyurethanes correspond to the following general formula:

$$R^1-[-NH-CO-OR^2]_n$$

wherein
$R^1$ represents an optionally substituted aromatic hydrocarbon group having 5 to 18 carbon atoms, or optionally substituted diphenylmethane, and/or optionally substituted polymeric diphenylmethane linked with methylene groups;
$R^2$ represents an alkyl group having 2 or 3 carbon atoms; and
n stands for an integer greater than 1.

The substituents for the aromatic hydrocarbon group $R^1$ may be alkyl groups having from 1 to 12 carbon atoms.

The following are preferred examples of aromatic di- and/or polyurethanes: O-ethyl-, O-propyl- and O-isopropylurethanes based on various di- and/or polyamines or mixtures of di- and/or triamines such as m-phenylene-, p-phenylene-, 1,5-naphthylene-, 2,7-naphthylene- and 2,4-tolylenediamine and mixtures of 2,4- and 2,6-tolylene-diamine, of 2,2'-, 2,4'- and 4,4'-diaminodiphenylmethane, polyphenylene-polymethylene polyamines, and mixtures thereof, isomeric mixtures of methyl(diaminodiphenylmethane), and methyl(triaminodiphenylmethane), and mixtures thereof.

Suitable starting materials for the process according to the invention include primary amines corresponding to the general formula:

$$R^1(NH_2)_n$$

wherein
$R^1$ represents an optionally substituted aromatic hydrocarbon group having 5 to 18 carbon atoms, or optionally substituted diphenylmethane, and/or optionally substituted polymeric diphenylmethane linked with methylene groups; and
n stands for an integer greater than 1.

The substituents for the aromatic hydrocarbon group $R^1$ may be alkyl groups having from 1 to 12 carbon atoms.

The following di- and/or polyamines are particularly suitable: m-Phenylenediamine, p-phenylenediamine, 1,5- and 2,7-diaminonaphthalene, 2,4-tolylenediamine, 2,6-tolylene-diamine, and mixtures thereof, 2,2'-, 2,4'- and 4,4'-diaminodiphenylmethane (MDA), and mixtures thereof, mixtures of diaminodiphenylmethane and polyphenyl-polymethylene polyamines ("Polymer MDA"), isomeric mixtures of diaminomethyldiphenylmethane, triaminomethyl-diphenylmethane, and mixtures thereof.

The carbamates used may be ethyl, propyl or isopropyl carbamate. They are preferably used in their pure form, although unpurified carbamates as obtained from the reaction of urea with alcohols may also be used. The carbamates may also be prepared in situ from urea and alcohols.

The solvents used may be organic solvents. Preferably low boiling alcohols are used as solvents. In this case the reaction is carried out under pressure. In particular, the alcohols with 2 or 3 carbon atoms which correspond to the carbamates are used. If, however, the reaction is carried out under normal pressure, then high boiling, preferably aprotic polar solvents are used, e.g. dimethylformamide or dimethyl-acetamide.

Generally, the reaction is carried out without catalysts, but it may be accelerated with catalysts known in the art.

The pressure during the reaction depends upon the reaction temperature and the method employed. The reaction may be carried out at normal pressure using high boiling solvents or at elevated pressure using low boiling solvents, for example low boiling alcohols as mentioned above. Preferably, the reaction is carried out at its autogenous pressure, and continuously or intermittently.

The reaction is preferably carried out at elevated temperatures of from 120° to 350° C., and most preferably at temperatures of from 180° to 220° C.

To carry out the reaction, the aromatic di- and/or polyamines and the carbamates are heated to the reaction temperature, optionally in the presence of solvents, and preferably in a molar ratio (amino group:carbamate) of from 1:2 to 1:50 (more preferably from 1:10 to 1:30), and then ammonia is distilled from the reaction mixture, optionally together with the solvent. As mentioned above, the carbamate may be prepared in situ from urea and low boiling alcohols. In this case, the above-mentioned molar ratios also apply to the system of aromatic di- and/or polyamine to urea/alcohol. That is, from about 2 to 50 mol, preferably from about 10 to 30 mol, of urea, and from about 2 to 50 mol, preferably from about 10 to 30 mol, of alcohol, are required per mol of aromatic amino groups. It is advisable, however, to use the alcohol as a solvent if the carbamate is to be prepared in situ from urea and alcohol.

One particularly preferred embodiment of the reaction is carried out under pressure and the alcohols corresponding to the carbamates are used as solvents. The ammonia formed in the reaction is distilled off together with the alcohol used as solvent, and the alcohol losses are replaced. The required pressure is adjusted by a pressure regulating valve.

Pure ammonia may, of course, be distilled off through a column under pressure. In that case, replacement of the alcohol may be omitted.

In general, the proportion of the solvent is from about 5 to 90% by weight, and preferably from about 10 to 50% by weight, based on the whole reaction mixture.

The reaction times are from about 1 to 20 hours, and preferably about from 5 to 10 hours.

After termination of the reaction, the solvent is distilled off, optionally at reduced pressure. Then, the carbamate together with the by-products are separated from the remaining crude product by extraction with water.

This extraction is carried out by intensively mixing the crude product with water in a ratio of crude product to water of from about 0.2:1 to about 10:1, preferably from about 0.8:1 to about 2:1, at temperatures from about 20° to 200° C., preferably from about 50° to 100° C. Then, the mixture is cooled to temperatures of from about 0° to 100° C., preferably from about 20° to 70° C., optionally with stirring, and separating the phases. The extraction may be carried out several times with variation of the extraction conditions with regard to pressure, temperature and mixing ratios.

Solid products of the process, e.g. aromatic diurethanes, are filtered from the aqueous phase and are obtained after drying as highly pure urethanes which are suitable for the thermal decomposition of urethanes. Their purity may, if desired, be further increased by recrystallization from organic solvents. Organic solvents include, preferably, aromatic hydrocarbons such as benzene, toluene, xylene, or mixtures thereof. This recrystallization is performed, optionally, in the presence of surface-active substances such as active charcoal, Fuller's earth, bleaching earth, aluminium oxide, alumino-silicate and zeolithe.

Liquid products produced by the process, e.g. mixtures of di- and/or polyurethanes, separate from the aqueous phase due to their different densities, and may be removed in this way. Their purity may also be improved by contact with the above-mentioned surface active substances.

The products of the process are generally obtained as analytically pure substances.

The aqueous phase is cooled to temperatures from $-5°$ to 20° C., optionally with stirring. This results in the separation of a mixture composed of carbamate, aminourethanes, urea urethanes, and oligo- and polyureas, and, optionally, small quantities of the starting amine and di- and/or polyurethanes. The mixture is either filtered off or separated, depending on the aggregate state, and may be returned to the reaction after drying, and, optionally, after the addition of fresh aromatic di- and polyamines and carbamates, optionally, together with alcohol. The product yield may thereby be increased.

The aqueous mother liquor left after separation of the mixture may also be used for the extractive purification of the reaction product, optionally, as a mixture with fresh water or the other aqueous phases mentioned above.

The invention will now be illustrated with the aid of the following Examples. All percentages are percentages by weight unless otherwise indicated.

EXAMPLES

Example 1

Preparation of 2,4-bis-(ethoxycarbonylamino)-toluene 122 g (1 mol) of 2,4-Diaminotoluene and 1782 g (20 mol) of ethyl carbamate are heated to 200° C. in the presence of 320 g of ethanol, with stirring, in a 5-liter stirrer autoclave, and 1300 ml of an ammonia/ethanol mixture are distilled off per hour. The autoclave is adjusted to a pressure of from 6 to 10 bar by means of a control valve and the ethanol concentration is kept constant by pumping in fresh ethanol. After a reaction time of 5 hours, the autoclave is left to cool down, emptied, and the alcohol is distilled at 40° to 90° C./90 mbar. The distillation residue (1224 g) is taken up with 1200 g of water at 95° C. and intensively stirred. 260 g of 2,4-bis-(ethoxycarbonylamino)-toluene precipitate after cooling of the solution to 40° C. and are filtered off. The 2,4-bis-(ethoxycarbonylamino)-toluene is again taken up with 300 g of boiling water, and reprecipitated at 40° C. 170.4 g (64.1% of theoretical) of 2,4-bis-(ethoxycarbonylamino)-toluene are obtained after drying over night in a drying cupboard at 90° C./100 mbar.

Elementary analysis (DUMAS):

$C_{13}H_{18}N_2O_4$ (266.30) Calculated: C:58.6% H:6.8% N:10.5% Found: C:58.5% H:6.8% N:10.7%

Example 2

Preparation of 4,4'-bis-(ethoxycarbonylamino)-diphenylmethane 198 g (1 mol) of 4,4'-Diaminodiphenylmethane, 1782 g (20 mol) of ethyl carbamate and 1200 g of ethanol are heated to 200° C. with stirring in a 5-liter stirrer autoclave. The pressure is adjusted to about 16 bar by means of a control valve so that 1500 ml of an ammonia/ethanol mixture distill off per hour into a receiver cooled with brine. The quantity of ethanol lost is replaced by means of a pump. The autoclave is cooled to 60° C. after 5 hours and emptied. Ethanol is distilled off under vacuum. The solid reaction product is washed twice with 1630 g and 900 g of water, respectively, at 60° C., dehydrated azeotropically with toluene, and recrystallized in the presence of 100 g of bleaching earth (Tonsil K10 ®, Südchemie). 246.0 g (71,9 % of the theory) of 4,4'-bis-(ethoxycarbonylamino)-diphenylamine having a melting point of 133° C. are obtained after drying over night in a drying cupboard at 90° C./100 mbar.

Elementary analysis (DUMAS):

$C_{19}H_{22}N_2O_4$ (342.40) Calculated: C: 66.7% H: 6.5% N: 8.2% Found: C: 66.8% H: 6.5% N: 8.2%

The purified wash waters are cooled to −2° C. 860 g of solid separate, consisting of 92.8% by weight of ethyl carbamate, 4.4% by weight of 4,4'-bis-(ethoxycarbonylamino)-diphenylmethane, 1.0% by weight of aminourethane, and 0.8% by weight of urea urethane.

Example 3

Return of by-product and ethyl carbamate 198 g of Diaminodiphenylmethane are reacted with 922 g of fresh ethyl carbamate and 860 g of the ethyl carbamate-containing solid obtained from Example 2, in the presence of 1200 g of ethanol as described in Example 2. After the product has been worked up by the same method, 270.0 g (78.9% of the theory) of 4,4'-bis-(ethoxycarbonylamino)-diphenylmethane are isolated with a degree of purity of 99,4 % by weight (analysing by high pressure liquid chromatography) and a melting point of 132° C.

Example 4

Preparation of polyphenylene-polymethylene-polyethylurethane ("Polymer MDU")

106.5 g of Polyphenylene polymethylene polyamine ("Polymer-MDA"), 2228.0 g of ethyl carbamate and 320 g of ethanol are heated to 200° C. with stirring in a 5-liter stirrer autoclave. The pressure in the autoclave is adjusted to 6 to 10 bar by means of a pressure control valve so that an ammonia/ethanol mixture distills off into a brine cooled receiver at the rate of 1300 ml/h. The ethanol content in the autoclave is kept constant by pumping ethanol into the autoclave through a membrane pump. After a reaction time of 5 hours, the reaction is terminated, and the autoclave is cooled and emptied. The alcohol used as solvent is removed by distillation at 40° to 90° C. and 90 mbar, and a residue of 1308 g is obtained which is then extracted with 1300 g of water at 95° C. in a separating funnel. 265 g of polymer-MDU is obtained after phase separation, and is extracted again by the same procedure with 250 g of water. 500 ml of toluene and 30 g of bleaching earth (Tonsil K10 ®, Südchemie) are then added to the product, and the product is dehydrated azeotropically. Tonsil K10 ® is filtered off through a suction filter and the filtrate is concentrated by evaporation in a rotary evaporator. The yield of polyphenylene polymethylene polyethylurethane ("Polymer MDU") obtained as a highly viscous product is 126.1 g. The product contains only 0,1% by weight of unreacted amino groups.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of highly pure aromatic diurethanes and/or polyurethanes comprising the steps of
   a) reacting
      1) the corresponding aromatic diamines and/or polyamines, with
      2) an excess of unsubstituted carbamates, with the release of ammonia,
   b) removing any solvents from the reaction mixture which were used in the reaction, and
   c) purifying the resultant aromatic diurethanes and/or polyurethanes by extraction with water.

2. The process of claim 1 wherein from 2 to 50 moles of component a)2) said unsubstituted carbamates are used per mole of amino groups in component a)1) said aromatic diamines and/or polyamines.

3. The process of claim 1 wherein from 10 to 30 moles of component a)2) said unsubstituted carbamates are used per mole of amino groups in component a)1) said aromatic diamines and/or polyamines.

4. The process of claim 1 wherein component a)2) said carbamates are selected from the group consisting of ethyl carbamate, propyl carbamate, isopropyl carbamate, and mixtures thereof.

5. The process of claim 1 wherein component a)2) said carbamates consist of unpurified carbamates obtained from the reaction of urea with the corresponding alcohol.

6. The process of claim 1 wherein component a)2) said carbamates consist of carbamates obtained from the reaction of urea with the corresponding alcohol and are formed in situ in the reaction of said corresponding aromatic diamines and/or polyamines with said unsubstituted carbamates.

7. The process of claim 1 wherein b) said removing step of any solvents is by distillation.

8. The process of claim 1 wherein c) said purifying step of the resultant aromatic diurethanes and/or polyurethanes by extraction comprises the steps of:
   c1) intensively mixing the reaction mixture with water at 20° to 200° C., in a ratio of mixture to water of from 0.2:1 to 10:1,
   c2) cooling the mixture to temperatures of from 0° to 100° C., and
   c3) separating off the resultant aromatic diurethanes and polyurethanes as either a liquid or a solid phase.

9. The process of claim 8 wherein
   c1) said mixing step is at a temperature of 50° to 100° C., in a ratio of from 0.8:1 to 2:1, and
   c2) said cooling step is at a temperature of from 20° to 70° C.

10. The process according to claim 1 additionally comprising:

d) drying the resultant aromatic diurethanes and/or polyurethanes.

11. The process according to claim 1 additionally comprising:
   e) recrystallizing the resultant aromatic diurethanes and/or polyurethanes from an organic solvent.

12. The process according to claim 11 wherein said organic solvent is an aromatic hydrocarbon.

13. The process according to claim 12 wherein said aromatic hydrocarbon is selected from the group consisting of benzene, toluene, xylene, and mixtures thereof.

14. The process according to claim 11 wherein e) said recrystallizing step is done in the presence of a surface-active substance.

15. The process according to claim 14 wherein said surface-active substance is selected from the group consisting of active charcoal, Fuller's earth, bleaching earth, aluminum oxide, aluminosilicate, and zeolite.

16. The process according to claim 1 additionally comprising:
   f) cooling the remaining aqueous phase from c) said purifying step to a temperature of from −5° to 20° C., optionally, with stirring,
   g) separating the mixture of carbamate, aminourethanes, urea urethanes, oligoureas and polyureas, and optionally, diamines, and/or polyamines and diurethanes and/or polyurethanes from the mother liquor,
   h) optionally, drying said separated mixture, and
   i) returning said separated mixture to said reaction step, optionally together with alcohols.

17. The process according to claim 16 wherein the mother liquor obtained from g) said separation step is used as the aqueous phase for the extraction in c) said purifying step, optionally, together with fresh water.

* * * * *